United States Patent [19]

Sunagawa et al.

[11] Patent Number: 4,556,514

[45] Date of Patent: Dec. 3, 1985

[54] 4-CARBOXY AZETIDINONE COMPOUNDS AND PRODUCTION THEREOF FROM DIKETENE AND A SCHIFF BASE

[75] Inventors: Makoto Sunagawa; Koshiro Goda; Masao Enomoto; Akira Sasaki, all of Osaka, Japan

[73] Assignee: Sumitomo Chemical Company, Limited, Osaka, Japan

[21] Appl. No.: 541,648

[22] Filed: Oct. 13, 1983

[30] Foreign Application Priority Data

Oct. 13, 1982 [JP] Japan .................. 57-180268
Nov. 6, 1982 [JP] Japan .................. 57-194894
Jul. 28, 1983 [JP] Japan .................. 58-139068

[51] Int. Cl.$^4$ ........................... C07D 205/08
[52] U.S. Cl. ................................ 260/239 A
[58] Field of Search .................. 260/239 A, 245.3

[56] References Cited

FOREIGN PATENT DOCUMENTS 78026   5/1983  European Pat. Off. .
55-111463 8/1980 Japan .
56-142259 11/1981 Japan .
57-98257  6/1982 Japan .

OTHER PUBLICATIONS

Shiozaki et al., Tet. Letters 22, 5205, (1981).
Hirai et al., Tet. Letters 23, 4025, (1982).
Neider et al., Tet. Letters 23, 2293, (1982).
Sankyo et al., Chem. Abs. 94, 103147y, (1980).
Sankyo et al., Chem. Abs. 96, 85334s, (1981).
Sankyo et al., Chem. Abs. 98, 72422k.
Hagemeyer et al., Chem. Abs. 43, 839e, (1949).
Kato et al., Chem. Pharm. Bull. 24, 356, (1976).

Primary Examiner—Mark L. Berch
Attorney, Agent, or Firm—Sughrue, Mion, Zinn, Macpeak, and Seas

[57] ABSTRACT

β-Lactam compounds which are useful as intermediates for the production of carbapenem or penem derivatives and a process for producing the same. The process comprises reacting a Schiff base with diketene in the presence of an imidazole, reducing the acetyl group of the resulting N-protected-3-acetyl-2-azetidinone-4-carboxylic acid ester, and removing the protecting group for a carboxyl group from the resulting 3-(1-hydroxyethyl)-2-azetidinone-4-carboxylic acid derivative.

11 Claims, No Drawings

4-CARBOXY AZETIDINONE COMPOUNDS AND PRODUCTION THEREOF FROM DIKETENE AND A SCHIFF BASE

FIELD OF THE INVENTION

This invention relates to novel β-lactam compounds and a process for producing the same which are important intermediates for producing carbapenem or penem derivatives.

BACKGROUND OF THE INVENTION

Since the discovery of thienamycin, it has been recently proved that carbapenem or penem derivatives having a 1-hydroxyethyl group at the 6-position of their skeleton possess excellent antimicrobial activities and are useful as medicines, and studies on syntheses thereof have been extensively conducted.

The present inventors have made various investigations to develop an effective process for producing carbapenem or penem derivatives having a 1-hydroxyethyl group at their 6-position and, as a result, found that 3-acetyl-2-azetidinone-4-carboxylic acid derivatives or 3-(1-hydroxyethyl)-2-azetidinone-4-carboxylic acid derivatives that are important intermediates for these carbapenem or penem derivatives can easily and effectively be produced, and that these derivatives can be converted into the desired carbapenem or penem derivatives.

A conventional process for preparing N-protected-3-acetyl or 3-(1-hydroxyethyl)-2-azetidinone-4-carboxylic acid derivatives comprises introducing an acetyl group or a 1-hydroxyethyl group to the 3-position of 3-unsubstituted 2-azetidinone, for example, by aldol condensation in the presence of a strong base as disclosed in *Tetrahedron Letters*, 23 (22), 2293 (1982), and the like. However, such known processes are disadvantageous in terms of number of steps involved, workability, etc.

To the contrary, the process of the present invention makes it possible to produce N-protected-3-acetyl or 3-(1-hydroxyethyl)-2-azetidinone-4-carboxylic acid derivatives at high efficiency through very simple operations.

SUMMARY OF THE INVENTION

This invention relates to an N-protected-3-acetyl-2-azetidinone-4-carboxylic acid ester represented by the formula (II):

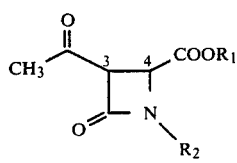

(II)

wherein $R_1$ represents a protecting group for a carboxyl group and $R_2$ represents a protecting group for a nitrogen atom, and a process for producing the same.

Further, this invention relates to a process for producing N-protected-3-(1-hydroxyethyl)-2-azetidinone-4-carboxylic acids represented by the formula (IV):

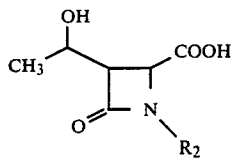

(IV)

wherein $R_2$ is as defined above, which comprises reacting a Schiff base represented by the formula (I):

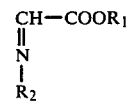

(I)

wherein $R_1$ and $R_2$ are as defined above, with diketene in the presence of an imidazole to form an N-protected-3-acetyl-2-azetidinone-4-carboxylic acid ester represented by the above-described formula (II), reducing the acetyl group of the resulting ester to obtain a 3-(1-hydroxyethyl)-2-azetidinone-4-carboxylic acid derivative represented by the formula (III):

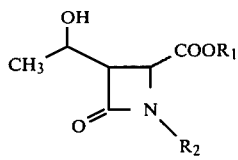

(III)

wherein $R_1$ and $R_2$ are as defined above, and removing the protecting group for the carboxyl group $R_1$ from the resulting derivative of the formula (III).

DETAILED DESCRIPTION OF THE INVENTION

In the present invention, the protecting group for a carboxyl group as represented by $R_1$ is not particularly limited as long as it is a group that serves as a protecting group for a carboxyl group and includes, for example, an alkyl group, an alkenyl group, a substituted lower alkyl group, an aryl group, etc.

The alkyl groups include, for example, alkyl groups having a straight chain, branched chain or cyclic alkane structure and more particularly lower to middle chain alkyl groups having 1 to 7 carbon atoms and having a primary carbon atom at their α-position, such as a methyl group, an ethyl group, an n-propyl group, an n-butyl group, a 2-methylpropyl group, an n-pentyl group, a 2-methylbutyl group, a 3-methylbutyl group, an n-hexyl group, a 2-ethylbutyl group, a 2-methylhexyl group, a 3-methylhexyl group, a 4-methylhexyl group, a cyclopropylmethyl group, a cyclohexylmethyl group, a cyclopentylmethyl group, etc.

The alkyl groups further include lower to middle chain alkyl groups having a secondary carbon atom at their α-position, such as an isopropyl group, a 1-methylethyl group, a 1-methylpropyl group, a 1-methylbutyl group, a 1-methylpentyl group, a 1-ethylpropyl group, a 1-ethylbutyl group, a 1-cyclopentylethyl group, a 1-cyclohexylmethylethyl group, etc. Such alkyl groups having a secondary carbon atom at their α-position can be represented by the formula (V):

wherein $R_3$ and $R_4$ each represents a lower alkyl group, a cyclic lower alkyl group or a cyclic lower alkyl-lower alkyl group. The term "lower alkyl" herein used means straight or branched chain alkyl groups having 1 to 5 carbon atoms; the term "cyclic lower alkyl group" means cyclic alkyl groups having 3 to 6 carbon atoms; and the term "cyclic lower alkyl-lower alkyl group" means alkyl groups having 1 to 5 carbon atoms and substituted with a cyclic alkyl group having 3 to 6 carbon atoms.

The alkyl groups also include cyclic alkyl groups such as a cyclopentyl group, a cyclohexyl group, a cycloheptyl group, a bicyclo[2,2,1]heptyl group, a bicyclo[3,1,1]heptyl group, a bicyclo[3,1,0]hexyl group, a bicyclo[2,2,2]octyl group, polycyclic condensed alkyl groups, etc., which may be substituted with a lower alkyl group; and alkyl groups having a tertiary carbon atom at their α-position, such as a t-butyl group, etc.

The alkenyl groups are those having structures corresponding to the above-described alkyl groups and also having a double bond and 3 or more carbon atoms. The alkenyl groups are not particularly restricted as far as they have ordinary physiochemical stability, but generally include an allyl group, a 2-methylallyl group, a 3-methylallyl group, etc.

The above-enumerated alkyl and alkenyl groups ($R_1$) additionally include those groups which form alcohols represented by the formula $R_1OH$ and having a terpene or steroid structure, such as menthol, borneol, isoborneol, picocampheol, cholesterol, testosterone, etc.

It is also possible that these alkyl groups and alkenyl groups have 8 to 30 carbon atoms, if necessary.

The substituted lower alkyl groups are those having 1 to 4 carbon atoms in the alkyl moiety, and the substituents in the substituted lower alkyl group are not particularly limited, but preferred examples of the substituted lower alkyl groups are mono- or diarylalkyl groups, halogen-substituted alkyl groups, alkoxy- or aralkoxy-substituted alkyl groups and the like.

The mono- or diarylalkyl groups can include groups represented by the formula (VI):

wherein $R_5$ represents an aryl group and $R_6$ represents a hydrogen atom, a lower alkyl group or an aryl group. The aryl group includes, for example, a phenyl group, a naphthyl group and a phenyl group substituted with a lower alkyl group or lower alkoxy group each having 1 to 4 carbon atoms, a nitro group, a nitrile group, a halogen atom, etc. The lower alkyl group for $R_6$ include, for example, a methyl group, an ethyl group, an n-propyl group, an isopropyl group, an n-butyl group, etc.

More particularly, examples of the monoarylalkyl groups include a benzyl group, a p-methylbenzyl group, an o-methylbenzyl group, a 2,4-dimethylbenzyl group, a p-methoxybenzyl group, an o-methoxybenzyl group, a 2,4-dimethoxybenzyl group, a p-nitrobenzyl group, an o-nitrobenzyl group, a p-chlorobenzyl group, an o-chlorobenzyl group, a 2,4-dichlorobenzyl group, a p-cyanobenzyl group, an o-cyanobenzyl group, a 2-naphthylmethyl group, a 1-naphthylmethyl group, a 1-phenylethyl group, a 1-(o-methylphenyl)ethyl group, a 1-(p-methylphenyl)ethyl group, a 1-(2,4-dimethylphenyl)ethyl group, a 1-(o-methoxyphenyl)ethyl group, a 1-(p-methoxyphenyl)ethyl group, a 1-(p-nitrophenyl)ethyl group, a 1-(o-nitrophenyl)ethyl group, a 1-(o-chlorophenyl)ethyl group, a 1-(2,4-dichlorophenyl)ethyl group, a 1-(p-cyanophenyl)ethyl group, a 1-(2-naphthyl)ethyl group, a 1-(1-naphthyl)ethyl group, and a series of substituents having further increased carbon atom numbers such as a 1-phenylpropyl group.

Examples of the diarylalkyl groups include substituted or unsubstituted diphenylmethyl groups, such as a diphenylmethyl group, a di-p-anisylmethyl group, etc. The arylalkyl groups can further include a 2-phenylethyl group, a 3-phenylpropyl group and other phenyl groups having the above-described various substituents.

The halogen-, alkoxy- or aralkoxy-substituted alkyl groups can include, for example, lower alkyl groups having 1 to 3 carbon atoms and substituted with a halogen atom, a benzyloxy group or a lower alkoxy group having 1 to 3 carbon atoms, e.g., a 2,2,2-trichloroethyl group, a 2-iodoethyl group, a benzyloxymethyl group, a methoxymethyl group, etc.

The aryl group as a protecting group for a carboxyl group includes a substituted or unsubstituted phenyl group such as a phenyl group, a p-nitrophenyl group, a p-methoxyphenyl group, etc.

The group $R_2$ representing a protecting group for a nitrogen atom is not particularly limited and any of usually employed protecting groups for a nitrogen atom may be used. Examples for the group $R_2$ include, for example, a mono- or diarylalkyl group, an aryl group, etc.

Examples of the arylalkyl group are substituted or unsubstituted benzyl groups, such as a benzyl group, a p-methoxybenzyl group, a 2,4-dimethoxybenzyl group, a p-nitrobenzyl group, and benzyl groups as enumerated above having their benzyl position substituted with a $C_1$–$C_4$ lower alkyl group.

Examples of the diarylalkyl groups are diphenylmethyl groups unsubstituted or substituted with a lower alkoxy group having 1 to 3 carbon atoms, such as a diphenylmethyl group, a di-p-anisylmethyl group, etc.

The aryl groups can include, for example, a phenyl group substituted with a lower alkoxy group having 1 to 3 carbon atoms, such as a p-methoxyphenyl group, etc.

The process of the present invention will now be illustrated in greater detail according to each step.

Firstly, the Schiff base represented by the above-described formula (I) is reacted with diketene in an inert solvent in the presence of an imidazole to obtain the 3-acetyl-2-azetidinone derivative represented by the above-described formula (II).

The imidazoles that can be used in this reaction include imidazole and various imidazole derivatives such as 2- or 4-lower alkyl-substituted imidazoles, e.g., 4-methylimidazole, 2-methylimidazole, etc., with imidazole or 4-methylimidazole being preferred.

The imidazoles can be used in an amount of from a catalytic amount to a large excess amount, but it is desirable to use the imidazoles in an amount of from 0.1 to 1.5 molar times that of the Schiff base.

The inert solvents preferably include aromatic hydrocarbons, e.g., benzene, toluene, xylene, etc.; halogenated hydrocarbons, e.g., dichloromethane, chloroform, 1,2-dichloroethane, etc.; and their mixtures. Other various solvents such as ethers, e.g., diethyl ether, tetrahydrofuran, dioxane, ethylene glycol dimethyl ether, etc.; nitriles, e.g., acetonitrile, etc.; aliphatic hydrocarbons, e.g., hexane, heptane, cyclohexane, pentane, etc.; dimethylformamide; dimethyl sulfoxide; and acetic acid esters, e.g., methyl acetate, ethyl acetate, etc., may also be employed.

It is possible to suppress or accelerate the reaction by cooling or heating and, in general, the reaction temperature ranges from −20° C. to 120° C. It is preferred to carry out the reaction at a temperature in the range of from −15° to 60° C. from the standpoint of operational workability.

After completion of the reaction, the reaction product can be isolated by usual organochemical means.

Then, the acetyl group of the 3-acetyl-2-azetidinone derivatives (II) thus obtained is reduced to obtain the 1-hydroxyethyl derivatives represented by the above-described formula (III).

The above reduction reaction can be carried out by various methods which are generally adopted for the reduction of a carbonyl group. For example, the reaction can be achieved in an inert solvent using, as a reducing agent, a boron hydride compound such as sodium borohydride, lithium borohydride, potassium borohydride, zinc borohydride, diboran, complexes of boran and various amines, e.g., a diisopropylamineboran complex, and the like. Further, the reduction can be carried out by adding a metal salt such as magnesium acetate, magnesium triflfuoroacetate, zinc chloride, etc., to the above reaction system as an auxiliary agent for the reaction. The reducing agent is required to be used in an amount enough for the reaction to sufficiently proceed. The reaction may be suppressed or accelerated by cooling or heating, but the reaction temperature generally ranges from −78° to 40° C.

The solvents which can be used in the reduction include ether solvents such as diethyl ether, tetrahydrofuran, dioxane, ethylene glycol dimethyl ether, etc.; alcohol solvents such as methanol, ethanol, isopropyl alcohol, etc.; water; and a mixture of these solvents. Aromatic hydrocarbons such as benzene, toluene, etc., and hydrocarbons such as cyclohexane, n-hexane, etc., may also be used.

The acetyl derivatives may also be converted into the desired 1-hydroxyethyl derivatives through a catalytic reduction method using a platinum type catalyst, etc.

After completion of the reaction, the resulting reaction product can be isolated by usual organochemical means.

Further, the carboxyl-protecting group $R_1$ of the ester derivatives of the formula (III) as above obtained is removed according to a usual manner thereby to produce the carboxylic acids represented by the above-described formula (IV).

The reaction for removal of $R_1$ can be carried out by various methods commonly employed for the conversion of an ester group to a carboxylic acid. For example, the reaction can be accomplished by a so-called alkali hydrolysis method in which the ester derivative of the formula (III) is reacted with a base, e.g., sodium hydroxide, sodium carbonate, potassium carbonate, sodium bicarbonate, etc., in the presence of water in an inert solvent, e.g., tetrahydrofuran, dioxane, methanol, ethanol or a mixture of these solvents. It is possible to suppress or accelerate the reaction by cooling or heating, but the reaction temperature is usually from −15° to 50° C. Further, the base is used in a catalytic amount to an excess amount and preferably in an amount of from 0.9 to 1.5 molar times that of the ester derivative.

If necessary, this reaction step can also be effected by a method wherein an acid, e.g., trifluoroacetic acid, formic acid, boron trifluoride etherate, etc., is used in the presence or absence of anisole, resorcin dimethyl ether, thioanisole, etc., or by a catalytic reduction method using a platinum or palladium type catalyst.

After completion of the reaction, the resulting reaction product can be isolated by usual organochemical means.

The steric structure of the compounds represented by the formulae (II) and (III) which can be obtained according to the present invention will hereinafter be described.

In the compounds of the formula (II) obtained according to the process of this invention, there are two steric configurations, i.e., cis- and trans-configurations, between the 3-acetyl group and the 4-ester group thereof to form steric isomers, and both of the 3- and 4-positions are asymmetric carbon atoms to form optical isomers. Although all of these isomers are represented by a single formula (II) for the sake of convenience, the scope of the present invention is not limited to the compounds represented by such a formula.

However, compounds having a trans-configuration between the 3-acetyl group and the 4-ester group of the $\beta$-lactam ring can be obtained at a very high selectivity by the process of the invention in which the above-described compound (I) is used as a starting material.

With respect to the optical isomers, when the Schiff base represented by the formula (I) contains no asymmetric carbon atom in the group $R_1$, the reaction with diketene produces a racemic 3-acetyl-2-azetidinone derivative (II).

On the other hand, the cases when the group $R_1$ contains at least one asymmetric carbon atom and also is a racemic $R_1$ are described below.

Referring only to the cases where the 3- and 4-positions of the following formula are in a trans-configuration, there are an S-configuration and an R-configuration at the 4-positioned asymmetric carbon atom.

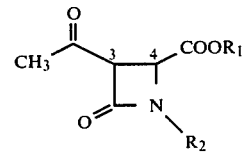

In addition, if $R_1$ contains only one asymmetric carbon atom, S- and R-configurations are also present. In these cases, therefore, the resulting products include four isomers of (S,S), (S,R), (R,S) and (R,R), expressing as (configuration of the 4-position of a lactam ring, configuration of $R_1$). The (S,S)-compounds and (R,R)-compounds, or the (S,R)-compounds and (R,S)-compounds are enantiomers with each other, respectively. For example, the (S,S)-compounds and (S,R)-compounds, or the (R,S)-compounds and (R,R)-compounds are diastereomers with each other, respectively. Diastereomers are generally distinguishable from each other by nuclear magnetic resonance spectra, high performance liquid chromatography (HPLC) or silica gel thin layer chromatography, etc. For instance, in the cases when diastereomers can be separated from each other by HPLC, a mixture of the (S,S)-compound and the (R,R)-compound and a mixture of the (S,R)-compound and the (R,S)-compound show a single peak, respectively, resulting in obtaining a chart showing two peaks. The ratio of these two peaks varies depending on the group R₁ used, but the production proportion of the (S,S)-compound to the (R,R)-compound or the production proportion of the (S,R)-compound to the (R,S)-compound is usually 1:1.

Accordingly, when R₁ forms optical isomers, e.g., when R₁ is in an S-configuration, two isomers, i.e., an (S,S)-compound and an (R,S)-compound, are obtained. Since the production proportion of (S,S)-compound to (R,S)-compound varies depending on the type of the group R₁ as mentioned above, one of the diastereomers can be predominantly produced.

The cases where the group R₁ contains at least one asymmetric carbon atom and is optically active are then described below. As set forth above, there are obtained two isomers represented by the following formulae (IIa) and (IIb):

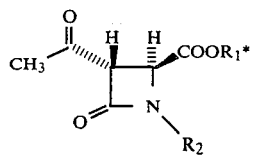
(IIa)

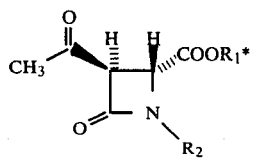
(IIb)

wherein R₁* means the above-identified group R₁ which contains at least one asymmetric carbon atom and is optically active, and R₂ is as defined above. The compounds of the formulae (IIa) and (IIb) are diastereomers with each other and can be separated by a usual organochemical means. The production proportion of (IIa) and (IIb) varies depending upon the type of the group R₁* or its steric configuration, and the product is obtained as a mixture wherein either of the compound (IIa) or (IIb) is produced in a proportion predominant over the other. Further, as described above, these mixtures can be separated by usual organochemical means, such as chromatography, e.g., thin layer chromatography using silica gel, alumina, etc., column chromatography, high performance liquid chromatography (HPLC), etc., crystallization, and the like. It is also possible that these diastereomers are reduced and, if necessary, the hydroxyl group is protected to obtain the derivatives represented by the formula (IIIa):

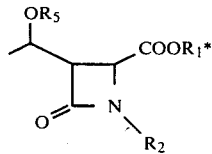
(IIIa)

wherein R₁* and R₂ are as defined above, and R₃ represents a hydrogen atom or a protecting group for a hydroxyl group, and then the resulting diastereomers of the formula (IIIa) are separated into each of the diastereomers.

The description will be directed more specifically to the compounds of the above-described formulae (IIa) and (IIb) wherein R₁* is a 1-(—)-menthyl group.

The compounds of the formulae (IIc) and (IId) below are mutual diastereomers and each of the diastereomer can be separated from their mixtures by usual organochemical means.

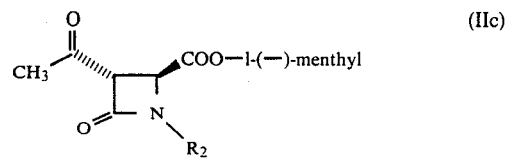
(IIc)

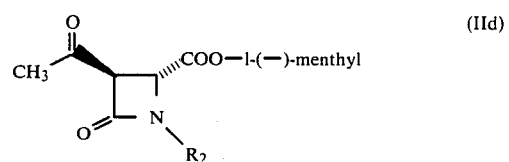
(IId)

wherein R₂ is as defined above.

In the above case, 4-(S)-derivatives of the formula (IIc) that are preferred intermediates in the production of carbapenem or penem derivatives having a strong antimicrobial activity such as thienamycin can be obtained as a major product.

The compounds of the formulae (IIc) and (IId) are separated as follows. For instance, a mixture of isomers represented by the following formulae (IIe) and (IIf) can be separated by crystallization.

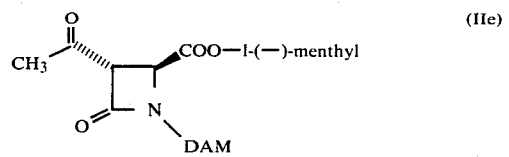
(IIe)

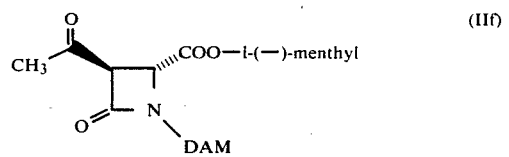
(IIf)

wherein DAM means a di(p-anisyl)methyl group represented by the formula:

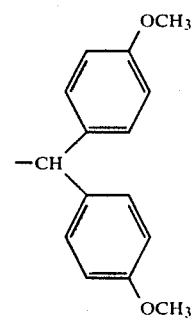

The solvents to be used for crystallization can include saturated hydrocarbon solvents, e.g., cycloheptane, cyclohexane, petroleum ether, n-hexane, etc.; aromatic hydrocarbons, e.g., benzene, toluene, etc.; alcohol solvents, e.g., methanol, ethanol, isopropyl alcohol, n-butanol, etc.; ether solvents, e.g., diethyl ether, etc.; halogenated alkyl type solvents, e.g., carbon tetrachloride, chloroform, methylene chloride, 1,2-dichloroethane, etc.; and mixtures of these solvents, with mixtures of a saturated hydrocarbon solvent and a halogenated alkyl type solvent or alcohol solvents being preferred.

The compounds of the formulae (IIe) and (IIf) can also be separated by high performance liquid chromatography.

In the 1-hydroxyethyl derivatives represented by the formula (III), the carbon atom to which a hydroxyl group is bonded is an asymmetric carbon atom and, therefore, there are steric and optical isomers. These isomers are represented by a single formula for the sake of convenience but the present invention is not limited thereto. The steric selectivity of these isomers varies depending on conditions for reduction, and proper conditions are selected according to the purpose so as to obtain a 1-hydroxyethyl derivative having one of the steric configuration as a main product. For example, in the case when the (3S,4S)-compound represented by the above-described formula (IIe) is reduced by a method of using sodium borohydride in isopropyl alcohol at room temperature, or by catalytic reduction using a platinum oxide-ethanol system, or by a method of using a diisopropylamine-boran complex in the presence of magnesium trifluoroacetate, a 1-hydroxyethyl derivative wherein the ratio of R and S of the asymmetric carbon atom to which a hydroxyl group is attached is about 3:5, about 1:9, or about 4:1, respectively, is obtained.

The β-lactam compounds of the above-described formula (IV) which are produced by the present invention are useful as intermediates for various antimicrobial carbapenem or penem derivatives.

For example, the compounds of the following formula (IVa) can be converted into the compounds (B) as follows, as disclosed in Japanese Patent Application Laid Open No. 99463/83:

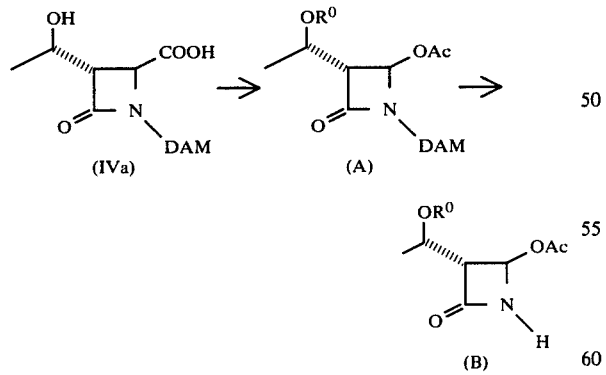

wherein DAM has the same meaning as defined above, and $R^0$ represents a hydrogen atom or a protecting group for a hydroxyl group. That is, the compound (IVa) can be converted into an acetoxy derivative (A) wherein $R^0$ is a hydrogen atom by reacting with lead tetraacetate. If necessary, the hydroxyl group of the compound (A) can be protected in a usual manner, such as by the reaction with a hydroxyl-protecting reagent, e.g., p-nitrobenzyl chloroformate, t-butyldimethylsilyl chloride, etc. The compound (B) can be obtained by, for example, treating the compound (A) with ceric ammonium nitrate in an inert solvent, such as water, acetonitrile, dimethylformamide, or a mixture thereof.

The β-lactam compound (B) as above obtained is known in literatures as an important intermediate for carbapenem derivatives or penem derivatives.

As described in the foregoing, the present invention provides a process for producing carboxylic acid derivatives represented by the formula (IV), which process comprises reacting diketene with a Schiff base represented by the formula (I) in the presence of an imidazole to prepare a 3-acetyl-2-azetidinone derivative represented by the formula (II), reducing the compound (II) to form a 1-hydroxyethyl-2-azetidinone derivative represented by the formula (III), and then removing a protecting group for a carboxyl group. The process of the present invention is very effective particularly due to its features that the 3-acetyl-2-azetidinone derivative (II) having one of configurations at the asymmetric carbon atom on the 2-azetidinone ring can be produced predominantly by using an optically active group for the group $R_1$ in the Schiff base (I) and that the optically active compound (II) can be separated and purified, if desired.

The Schiff base (I) can be prepared according to generally known methods, and several processes for preparing the starting materials therefor, i.e., glyoxylates, have been reported. For example, the glyoxylates can be synthesized as follows [Roczikі Chemii, 44 (11), 2161 (1970)]:

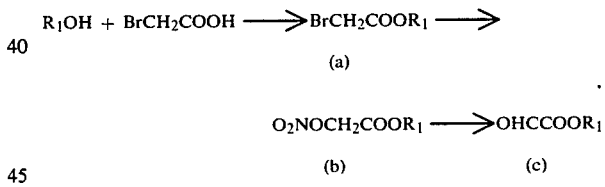

wherein $R_1$ is as defined above.

The bromoacetic ester (a) may also be synthesized by reacting an alcohol derivative with bromoacetyl bromide in the presence of a base such as triethylamine, dimethylaminopyridine, etc.

The present invention will now be illustrated in greater detail with reference to Examples and Reference Examples, but they are not to be construed as limiting the present invention.

In Examples and Reference Examples, the following abbreviations are used:

DAM: Di-p-anisylmethyl group

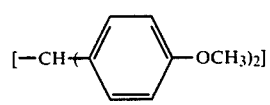

n-Bu: n-Butyl group
Men(l): l-(−)-Menthyl group

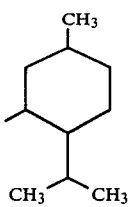

Men(d): d-(+)-Menthyl group
PMP: p-Methoxyphenyl group
PMB: p-Methoxybenzyl group
Bz: Benzyl group
Bor: l-(−)-Bornyl group

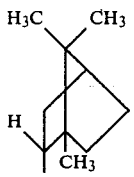

Cho: Cholestenyl group

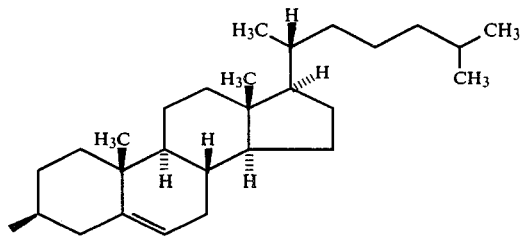

Further, the glyoxylates used in all Examples hereinafter given are hydrates.

EXAMPLE 1

(1-1a)

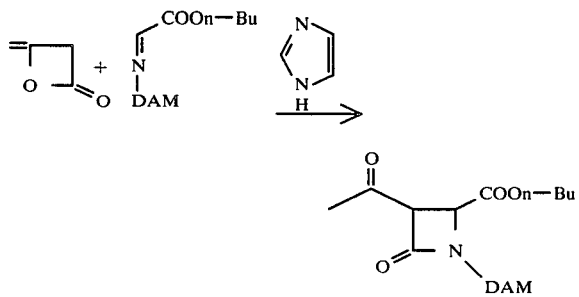

2.43 g (10 mM) of di-p-anisylmethylamine and 1.78 g (12 mM) of n-butyl glyoxylate were dissolved in 95 ml of dried toluene, and the resulting solution was azeotropically dehydrated to form a Schiff base. Dried toluene was added in an amount equivalent to that distilled off. 0.68 g (10 mM) of imidazole was then added thereto, and a solution of 1.01 g (12 mM) of diketene in 30 ml of dried toluene was added thereto dropwise at 50° C. over a period of 2 hours. After the mixture was stirred for 15 minutes, the reaction mixture was poured into a cold dilute hydrochloric acid solution, extracted with toluene, washed successively with 2N hydrochloric acid, a saturated sodium bicarbonate aqueous solution and a saturated sodium chloride aqueous solution, dried over sodium sulfate and distilled off under reduced pressure to remove the solvent. The resulting oily substance was separated and purified by silica gel column chromatography to obtain 3.86 g (88%) of 1-(di-p-anisylmethyl)-3-acetyl-4-n-butyloxycarbonyl-2-azetidinone. m.p.: 92.5°–94.0° C.

IR$_{max}^{nujol}$ (cm$^{-1}$): 1765, 1740, 1712, 1612, 1255, 1026, 818.

NMR δ(CDCl$_3$): 0.60–1.80 (7H, m), 2.28 (3H, s), 3.77 (6H, s), 3.77–4.15 (2H, m), 4.17 (1H, d, J=2 Hz), 4.40 (1H, d, J=2 Hz), 5.78 (1H, s), 6.60–7.40 (8H, m) ppm.

(1-1b)

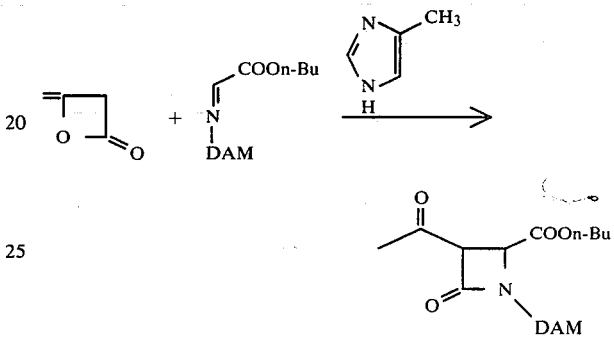

243 mg (1 mM) of di-p-anisylmethylamine and 178 mg (1.2 mM) of n-butyl glyoxylate were dissolved in 12 ml of dried toluene, and the solution was azeotropically dehydrated to form a Schiff base. Dried toluene was added to the mixture in an amount equivalent to that distilled off, and 82 mg (1 mM) of 4-methylimidazole was added thereto. A solution of 101 mg (1.2 mM) of diketene in 0.5 ml of dried toluene was then added thereto dropwise over a period of 20 minutes, followed by stirring the mixture for 3 hours. The reaction mixture was poured into a cold dilute solution of hydrochloric acid, extracted with toluene, washed successively with 2N hydrochloric acid, a saturated sodium chloride aqueous solution, a saturated sodium bicarbonate aqueous solution and a saturated sodium chloride aqueous solution, dried over sodium sulfate, and distilled off to remove the solvent. The resulting oily substance was separated and purified by silica gel thin layer chromatography to obtain 240 mg (55%) of 1-(di-p-anisylmethyl)-3-acetyl-4-n-butyloxycarbonyl-2-azetidinone.
This product showed the same IR and NMR data as those obtained in Example 1-1a.

(1-1c)

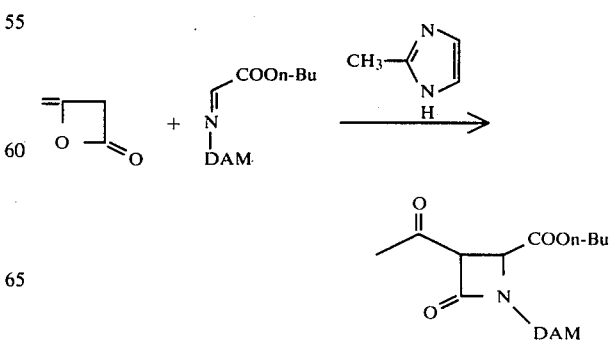

243 mg (1 mM) of di-p-anisylmethylamine and 178 mg (1.2 mM) of n-butyl glyoxylate were dissolved in 12 ml of dried toluene, and the resulting solution was azeotropically dehydrated to form a Schiff base. Dried toluene was added to the mixture in an amount equivalent to that distilled off. 82 mg (1 mM) of 2-methylimidazole was added thereto. A solution of 101 mg (1.2 mM) of diketene in 0.5 ml of dried toluene was added to the mixture dropwise at 50° C. over 20 minutes, followed by stirring for 2 hours, at 60° C. for 1 hour, and then at 80° C. for 1 hour. The resulting mixture was worked up and the product was separated and purified in the same manner as described in Example 1-1a thereby to obtain 24 mg (5%) of 1-(di-p-anisylmethyl)-3-acetyl-4-n-butyloxycarbonyl-2-azetidinone.

The IR and NMR data of this product were the same as those obtained in Example 1-1a.

(1-1d)

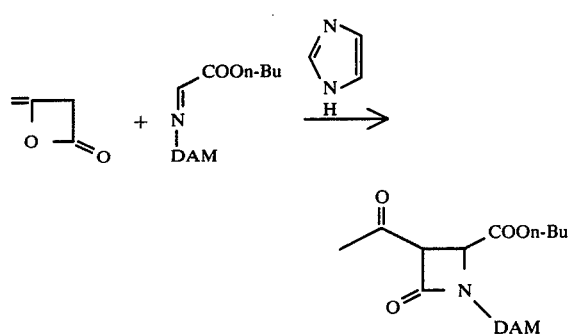

243 mg (1 mM) of di-p-anisylmethylamine and 178 mg (1.2 mM) of n-butyl glyoxylate were dissolved in 7 ml of dried toluene, and the resulting solution was azeotropically dehydrated to form a Schiff base. Dried toluene was added thereto in an amount equivalent to that distilled off, and 7 mg (0.1 mM) of imidazole was added to the mixture. A solution of 101 mg (1.2 mM) of diketene in 5.5 ml of dried toluene was added dropwise to the mixture at 50° C. over a period of 2 hours, and the mixture was stirred for 3 hours. The reaction mixture was worked up and the product was separated and purified in the same manner as described in Example 1-1a thereby to obtain 263 mg (60%) of 1-(di-p-anisylmethyl)-3-acetyl-4-n-butyloxycarbonyl-2-azetidinone.

The IR and NMR data of this product were the same as those obtained in Example 1-1a.

(1-1e)

243 mg (1 mM) of di-p-anisylmethylamine and 178 mg (1.2 mM) of n-butyl glyoxylate were dissolved in 7 ml of dried toluene, and the resulting solution was azeotropically dehydrated to form a Schiff base. Dried toluene was added thereto in an amount equivalent to that distilled off, and 34 mg (0.5 mM) of imidazole was then added thereto. A solution of 101 mg (1.2 mM) of diketene in 5.5 ml of dried toluene was added dropwise to the mixture at 50° C. over a period of 2 hours, followed by stirring for 1.3 hours. The resulting reaction mixture was worked up and the product was separated and purified in the same manner as described in Example 1-1a thereby to obtain 356 mg (81%) of 1-(di-p-anisylmethyl)-3-acetyl-4-n-butyloxycarbonyl-2-azetidinone.

The IR and NMR data of this product were the same as those obtained in Example 1-1a.

(1-2)

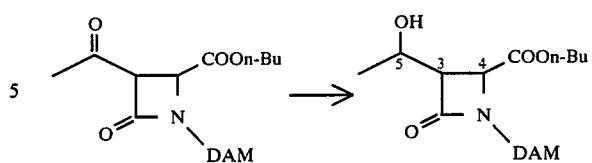

9 mg of sodium borohydride was added to a solution of 100 mg of 1-(di-p-anisylmethyl)-3-acetyl-4-n-butyloxycarbonyl-2-azetidinone in 1 ml of isopropyl alcohol at room temperature, and the mixture was stirred for 20 minutes. Water was added thereto, and the mixture was extracted with ethyl acetate, washed with water and dried over sodium sulfate. The solvent was distilled off, and the residue was purified by silica gel thin layer chromatography (multiple development method) thereby to obtain (3RS,4RS,5RS)-1-(di-p-anisylmethyl)-3-(1-hydroxyethyl)-4-n-butyloxycarbonyl-2-azetidinone [IR$_{max}^{CHCl_3}$ (cm$^{-1}$): 3450, 1740, 1607, 1300; NMR δ(CDCl$_3$): 1.35 (3H, d, J=6.4 Hz), 3.18 (1H, dd, J=2.4, 5.4 Hz), 3.79 (6H, s) ppm] and (3SR,4SR,5RS)-1-(di-p-anisylmethyl)-3-(1-hydroxyethyl)-4-n-butyloxycarbonyl-2-azetidinone [IR$_{max}^{CHCl_3}$ (cm$^{-1}$): 3450, 1740, 1603, 1292; NMR δ(CDCl$_3$): 1.27 (3H, d, J=6.4 Hz), 3.20 (1H, dd, J=2.4, 3.8 Hz), 3.78 (6H, s) ppm] at a proportion of about 5:3.

(1-3)

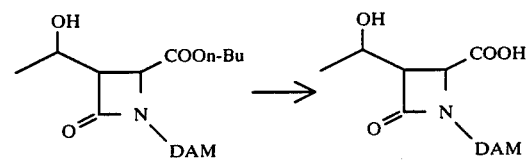

0.08 ml of a 1N aqueous solution of sodium hydroxide was added to a solution of 36 mg of 1-(di-p-anisylmethyl)-4-n-butyloxycarbonyl-3-(1-hydroxyethyl)-2-azetidinone in a mixed solvent of 1.3 ml of tetrahydrofuran and 1.1 ml of methanol at 15° C. after stirring the mixture for 5 minutes, the reaction mixture was diluted with a sodium chloride aqueous solution, neutralized with hydrochloric acid, extracted with methylene chloride, washed with water and dried over sodium sulfate. The solvent was distilled off, and the residue was separated and purified by silica gel thin layer chromatography to obtain 21 mg of 1-(di-p-anisylmethyl)-2-azetidinone-4-carboxylic acid.

IR$_{max}^{nujol}$ (cm$^{-1}$): 3250, 1750, 1723, 1305, 1179.

NMR δ(CDCl$_3$): 1.22 (3H, d, J=6 Hz), 3.18 (1H, m), 3.73 (6H, s), 4.10 (1H, d, J=2 Hz) ppm.

EXAMPLE 2

(2-1)

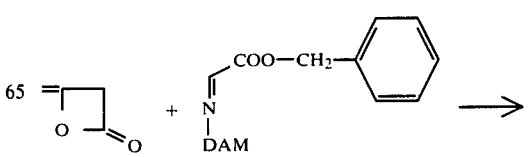

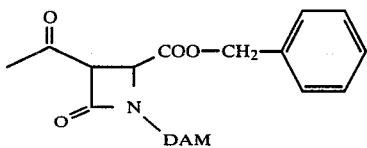

243 mg (1.0 mM) of di-p-anisylmethylamine and 218 mg (1.2 mM) of benzyl glyoxylate were dissolved in 12 ml of dried toluene, and the resulting solution was azeotropically dehydrated to form a Schiff base. Dried toluene was additionally added thereto in an amount equivalent to that distilled off, and 68 mg (1.0 mM) of imidazole was added to the mixture. A solution of 101 mg (1.2 mM) of diketene in 3 ml of dried toluene was added dropwise to the mixture at room temperature over a period of 10 minutes, followed by stirring for 1 day. The resulting reaction mixture was poured into cold dilute hydrochloric acid and extracted with toluene. The extract was washed successively with 2N hydrochloric acid, a saturated sodium chloride aqueous solution, a saturated sodium bicarbonate aqueous solution and a saturated sodium chloride aqueous solution and dried over sodium sulfate. The solvent was distilled off under reduced pressure, and the resulting oily substance was separated and purified by silica gel column chromatography to obtain 341 mg (72%) of 1-(di-p-anisylmethyl)-3-acetyl-4-benyloxycarbonyl-2-azetidinone.

m.p.: 135°–138° C.

IR$_{max}^{nujol}$ (cm$^{-1}$): 1762, 1739, 1720, 1602, 1241, 1180, 1019.

NMR δ(CDCl$_3$) 2.28 (3H, s), 3.73 (6H, s), 4.19 (1H, d, J=2 Hz), 4.45 (1H, d, J=2 Hz), 4.87 (2H, s), 5.80 (1H, s), 6.50–7.43 (8H, m) ppm.

(2-2)

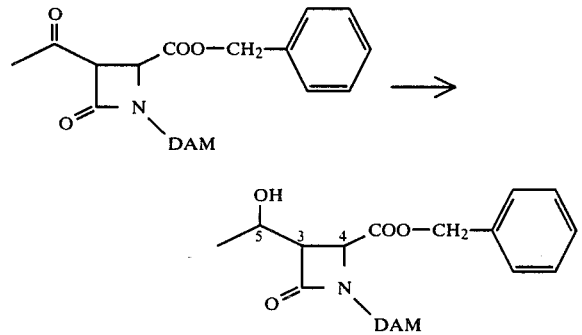

A solution of 3 mg of sodium borohydride in 0.1 ml of water was added to a solution of 40 mg of 1-(di-p-anisylmethyl)-3-acetyl-4-benzyloxycarbonyl-2-azetidinone in 1.5 ml of isopropyl alcohol at room temperature, and the mixture was stirred for 25 minutes. The reaction mixture was diluted with a saturated sodium chloride aqueous solution and ethyl acetate, washed successively with dilute hydrochloric acid, a saturated aqueous solution of sodium bicarbonate and a saturated aqueous solution of sodium chloride, and dried over sodium sulfate. The solvent was distilled off, and the residue was purified by thin layer silica gel chromatography (multiple development method) to obtain 13 mg of (3RS,4RS,5RS)-1-(di-p-anisylmethyl)-3-(1-hydroxyethyl)-4-benzyloxycarbonyl-2-azetidinone and 2 mg of (3SR,4SR,5RS)-1-(di-p-anisylmethyl)-3-(1-hydroxyethyl)-4-benzyloxycarbonyl-2-azetidinone.

(3RS,4RS,5RS)-Compound:

IR$_{max}^{neat}$ (cm$^{-1}$): 3420, 2950, 1740, 1605, 1505, 1240, 1170, 1012.

NMR δ(CDCl$_3$): 1.35 (3H, d, J=6 Hz), 3.20 (1H, dd, J=2, 5 Hz), 3.77 (6H, s), 3.93 (1H, d, J=2 Hz), 4.96 (2H, s), 5.12 (1H, s) ppm.

(3SR,4SR,5RS)-Compound:

NMR δ(CDCl$_3$): 1.24 (3H, d, J=6.4 Hz), 3.1–3.2 (1H, m), 3.76 (3H, s), 3.77 (3H, s), 4.14 (1H, d, J=2.6 Hz), 4.96 (2H, s), 5.84 (1H, s) ppm

EXAMPLE 3

(3-1a)

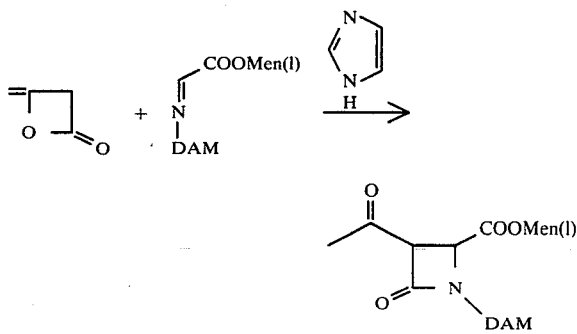

1.118 g (4.6 mM) of di-p-anisylmethylamine and 1.058 g (4.6 mM) of l-(−)-menthyl glyoxylate were dissolved in 43 ml of dried toluene, and the solution was azeotropically dehydrated to form a Schiff base. Dried toluene was added thereto in an amount equivalent to that distilled off. 313 mg (4.6 mM) of imidazole was then added thereto. A solution of 4.646 g (5.5 mM) of diketene in 14 ml of dried toluene was added dropwise to the mixture at 50° C. over a period of 2 hours, followed by stirring. The resulting reaction mixture was worked up and purified in the same manner as described in Example 1 thereby to obtain 1.965 g (82%) of 1-(di-p-anisylmethyl)-3-acetyl-4-l-(−)-menthyloxycarbonyl-2-azetidinone. The NMR spectrum of the product revealed that the production proportion of a 4-(S)-compound and a 4-(R)-compound was 3:2. Further, the 1-(di-p-anisylmethyl)-3-acetyl-4-l-(−)-menthyloxycarbonyl-2-azetidinone was fractionally recrystallized from an n-hexane-carbon tetrachloride solvent to separate the 4-(S)-compound thereby obtaining (3S,4S)-1-(di-p-anisylmethyl)-3-acetyl-4-l-(−)-menthyloxycarbonyl-2-azetidinone.

m.p.: 99°–100° C.

IR$_{max}^{nujol}$ (cm$^{-1}$): 1763, 1739, 1712, 1613, 1510, 1242, 1033, 818.

NMR δ(C$_6$D$_6$): 0.50–1.95 (19H, m), 1.94 (3H, s), 3.33 (6H, s), 4.00 (1H, d, J=2 Hz), 4.75 (1H, d, J=2 Hz), 4.40–5.05 (1H, m), 5.90 (1H, s), 6.60–7.60 (8H, m) ppm.

The filtrate thus separated was crystallized from an n-hexane-carbon tetrachloride solvent to obtain (3R,4R)-1-(di-p-anisylmethyl)-3-acetyl-4-l-(−)-menthyloxycarbonyl-2-azetidinone.

m.p.: 123°–125° C.

IR$_{max}^{nujol}$ (cm$^{-1}$): 1770, 1740, 1713, 1606, 1506, 1241, 1202, 1028, 822.

NMR δ(C$_6$D$_6$): 0.50–1.95 (19H, m), 1.93 (3H, s), 3.28 (3H, s), 3.30 (3H, s), 4.12 (1H, d, J=2 Hz), 4.75 (1H, d,

J=2 Hz), 4.40–4.85 (1H, m), 5.94 (1H, s), 6.50–7.50 (8H, m) ppm.

The two isomers as obtained above could also be separated by high performance liquid chromatography (HPLC) column: Lichrosorb SI-60; eluent: 0.5% isopropanol-n-hexane; flow rate: 1.5 ml/min; retention time: (4S)-compound; 46 minutes; (4R)-compound: 40 minutes).

(3-1b)

1 g of di-p-anisylmethylamine and 947 mg of l-(−)-menthyl glyoxylate were dissolved in 100 ml of dried toluene, and the resulting solution was azeotropically dehydrated to form a Schiff base. Toluene was additionally added thereto in an amount equivalent to that distilled off, and 336 mg of imidazole was added thereto. A solution of 519 mg of diketene in 5 ml of toluene was added dropwise to the resulting mixture at −10° to −12° C. over a period of 30 minutes. The mixture was stirred at that temperature for 3 hours and allowed to stand at room temperature overnight. To the reaction mixture was added an aqueous solution of sodium chloride, and the mixture was extracted with toluene, washed with dilute hydrochloric acid, water, a sodium bicarbonate aqueous solution and water in this order, and dried over sodium sulfate. The solvent was distilled off, and the residue was purified by silica gel column chromatography to obtain 1.93 g of 1-(di-p-anisylmethyl)-3-acetyl-4-(l-(−)-menthyloxycarbonyl)-2-azetidinone. High performance liquid chromatography (HPLC) revealed that the production proportion of a (4S)-compound and a (4R)-compound was about 2:1.

(3-1c)

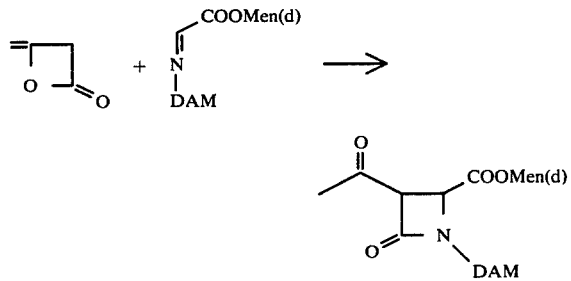

The same procedure as in Example 3-1a was repeated except for using 243 mg of di-p-anisylmethylamine, 230 mg of d-(+)-menthyl glyoxylate, 101 mg of diketene and 75 mg of imidazole to obtain 391 mg of 1-(di-p-anisylmethyl)-3-acetyl-4-d-menthyloxycarbonyl-2-azetidinone. By high performance liquid chromatography (HPLC), the proportion of a (4S)-compound and a (4R)-compound was found to be about 2:3. The NMR spectrum of the product was the same as that obtained in Example 3-1a.

(3-2a)

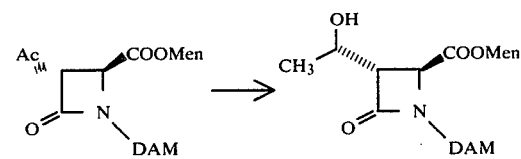

To a solution of 27 mg of (3S,4S)-1-(di-p-anisylmethyl)-3-acetyl-4-l-(−)-menthyloxycarbonyl-2-azetidinone in 0.5 ml of isopropyl alcohol was added a solution of 2 mg of sodium borohydride in 0.1 ml of water at room temperature, and the resulting mixture was stirred for 10 minutes. The reaction mixture was diluted by adding a saturated sodium chloride aqueous solution and ethyl acetate, washed successively with dilute hydrochloric acid, a saturated aqueous solution of sodium bicarbonate and a saturated sodium chloride aqueous solution, dried over sodium sulfate, and distilled to remove the solvent. The residue was purified by thin layer silica gel chromatography to obtain 23 mg of (3S,4S)-1-(di-p-anisylmethyl)-3-(1-hydroxyethyl)-4-l-(−)-menthyloxycarbonyl-2-azetidinone.

The high performance liquid chromatography analysis of the thus obtained product (column: Lichrosorb SI-60; eluent: 5% isopropanol-hexane) revealed that the proportion of the 5-(R)-compound and the 5-(S)-compound was about 3:5.

$IR_{max}^{CHCl_3}$ (cm$^{-1}$): 1735, 1600, 1500, 1350, 1168, 1022.

(3-2b)

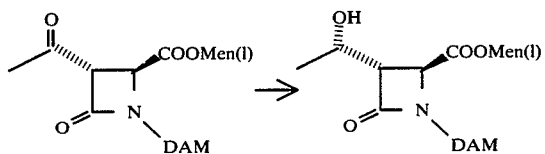

1 ml of ethanol was added to 10 mg of platinum dioxide. After stirring under a hydrogen stream, 30 mg of (3S,4S)-1-(di-p-anisylmethyl)-3-acetyl-4-l-(−)-menthyloxycarbonyl-2-azetidinone was added thereto. The resulting mixture was stirred under a hydrogen stream for 40 minutes, followed by filtration using Celite. The solvent was distilled off to obtain crude (3S,4S)-1-(di-p-anisylmethyl)-3-(1-hydroxyethyl)-4-l-(−)-menthyloxycarbonyl-2-azetidinone. The production proportion of the 5R-compound and the 5S-compound was found to be about 1:9 by HPLC.

Purification of the thus obtained mixture by silica gel thin layer chromatography (multiple development method) gave 21 mg of the 5S-compound.

$IR_{max}^{CHCl_3}$ (cm$^{-1}$): 1735, 1360; 1288, 1170, 1105.

NMR δ(CDCl$_3$): 1.33 (3H, d, J=6.2 Hz), 3.10 (1H, dd, J=2.2, 5.9 Hz), 3.78 (3H, s), 3.79 (3H, s), 5.80 (1H, s) ppm.

(3-2c)

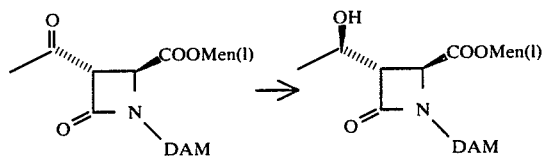

165 mg of (3S,4S)-1-(di-p-anisylmethyl)-3-acetyl-4-l-(−)-menthyloxycarbonyl-2-azetidinone was dissolved in 5 ml of dried diethyl ether and cooled with an acetone-dry ice bath. 425 mg of magnesium trifluoroacetate was added thereto, and a tetrahydrofuran solution containing about 100 mg of diisopropylamine-boran complex was added to the mixture. After stirring for 30 minutes, the resulting reaction mixture was diluted with dilute hydrochloric acid, extracted with ethyl acetate, washed with water, dried over sodium sulfate and distilled to remove the solvent thereby to obtain 158 mg of crude (3S,4S)-1-(di-p-anisylmethyl)-3-(1-hydroxyethyl)-4-l-(−)-menthyloxycarbonyl-2-azetidinone. The HPLC analysis of the product (column: Lichrosorb SI-60; eluent: 5% isopropanol-hexane) showed that the proportion of the (5R)-compound and the (5S)-compound was about 4:1.

Crystallization of the above-obtained mixture from diethyl ether-hexane gave crystals of the (5R)-compound.

m.p.: 105°–106° C.

IR$_{max}^{CHCl_3}$ (cm$^{-1}$): 1740, 1605, 1505, 1240, 1173.

NMR δ(CDCl$_3$): 0.5–2.0 (19H, m), 1.22 (3H, d, J=6 Hz), 3.12 (1H, br. t, J=3 Hz), 3.77 (6H, s), 4.07 (1H, d, J=3 Hz), 4.1–4.9 (2H, m), 5.80 (1H, s), 6.7–7.4 (8H, m) ppm.

(3-3)

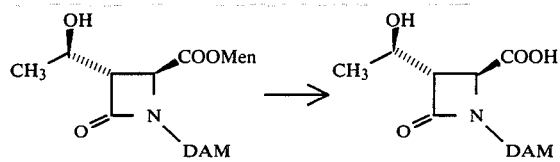

30 mg of (3S,4S,5R)-1-(di-p-anisylmethyl)-3-(1-hydroxyethyl)-4-1-(−)-menthyloxycarbonyl-2-azetidinone was dissolved in 0.9 ml of tetrahydrofuran and 0.45 ml of methanol. 0.06 ml of 1N sodium hydroxide was added dropwise thereto, and the mixture was stirred at room temperature for 4 hours, followed by neutralization with 1N hydrochloric acid. The reaction mixture was concentrated and diluted with diethyl ether. 0.1 ml of 1N sodium hydroxide was added thereto, and the mixture was extracted with water. To the extracted aqueous layer was added dropwise 0.12 ml of 1N hydrochloric acid. The mixture was extracted with diethyl ether, and the extract was washed with water, dried over sodium sulfate and distilled to remove the solvent thereby to obtain 22 mg of (3S,4S,5R)-1-(di-p-anisylmethyl)-3-(1-hydroxyethyl)-4-carboxyl-2-azetidinone.

IR$_{max}^{nujol}$ (cm$^{-1}$): 3250, 1750, 1723, 1515, 1305, 1250, 1177, 1030, 835.

NMR δ(CDCl$_3$): 1.22 (3H, d, J=6 Hz), 3.18 (1H, m), 3.72 (6H, s), 4.10 (1H, d, J=2 Hz), 5.75 (1H, s) ppm.

EXAMPLE 4

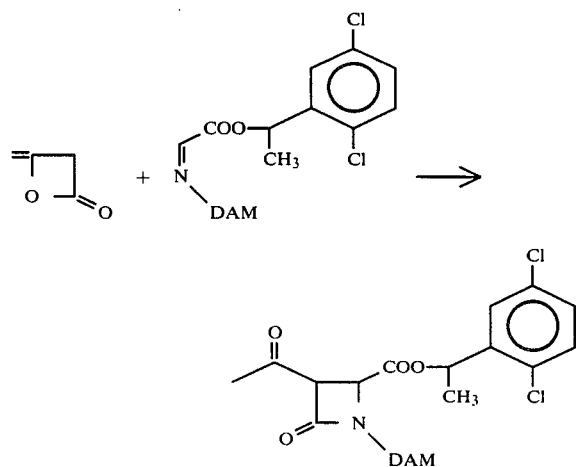

243 mg (1 mM) of di-p-anisylmethylamine and 265 mg (1 mM) of 1-(±)-(2,4-dichlorophenyl)ethyl glyoxylate were dissolved in 12 ml of dried toluene, and the resulting solution was azeotropically dehydrated to form a Schiff base. Dried toluene was added thereto in an amount equivalent to that distilled off, and 68 mg (1 mM) of imidazole was then added thereto. To the mixture was added dropwise a solution prepared by diluting 101 mg of diketene with 2 ml of dried toluene at 50° C. over a period of 20 minutes, followed by stirring at that temperature for 1 hour. A sodium chloride aqueous solution was added to the resulting reaction mixture, and the mixture was extracted with toluene, washed with water, and dried over sodium sulfate. The solvent was distilled off, and the residue was purified by silica gel chromatography to obtain two isomers in the amounts of 393 mg and 93 mg, respectively.

Isomer 1

IR$_{max}^{CHCl_3}$ (cm$^{-1}$): 1755, 1715, 1602, 1453, 1353, 1168, 1022.

NMR δ(C$_6$D$_6$): 1.12 (3H, d, J=6.6 Hz), 1.92 (3H, s), 3.87 (1H, d, J=2.2 Hz), 4.75 (1H, d, J=2.2 Hz) ppm.

Isomer 2

IR$_{max}^{CHCl_3}$ (cm$^{-1}$): 1758, 1715, 1605, 1352.

NMR δ(C$_6$D$_6$): 1.14 (3H, d, J=6.4 Hz), 1.89 (3H, s), 3.92 (1H, d, J=2.4 Hz), 4.81 (1H, d, J=2.4 Hz) ppm.

EXAMPLE 5

(a)

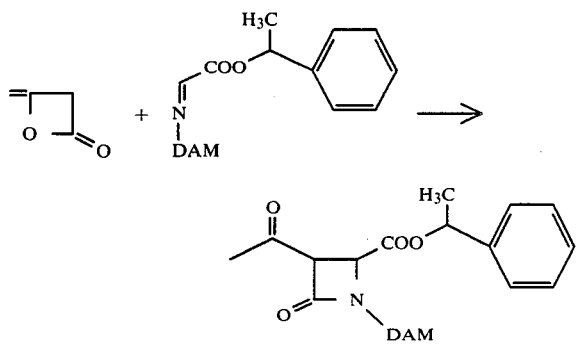

243 mg of di-p-anisylmethylamine and 196 mg of R-(+)-1-phenylethyl glyoxylate were dissolved in 12 ml of dried toluene, and the solution was azeotropically dehydrated to form a Schiff base. Dried toluene was added thereto in an amount equivalent to that distilled off, and 68 mg of imidazole was added thereto. A solution of 101 mg of diketene in 2 ml of toluene was then added dropwise to the mixture at 50° C. over a period of 20 minutes, followed by stirring at that temperature for 1 hour.

An aqueous sodium chloride solution was added to the reaction mixture, and the mixture was extracted with benzene, washed with water, dried over sodium sulfate and distilled to remove the solvent. The resulting residue was purified by silica gel column chromatography to obtain 334 mg of (3S,4S)-1-(di-p-anisylmethyl)-3-acetyl-4-(R-(+)-phenylethyloxycarbonyl)-2-azetidinone and 118 mg of (3R,4R)-1-(di-p-anisylmethyl)-3-acetyl-4-(R-(+)-phenylethyloxycarbonyl)-2-azetidinone.

(3S,4S)-Compound:

IR$_{max}^{CHCl_3}$ (cm$^{-1}$): 1753, 1713, 1600, 1345, 1163, 1018.

NMR δ(C$_6$D$_6$): 1.21 (3H, d, J=6.6 Hz), 1.84 (3H, s), 3.94 (1H, d, J=2.2 Hz), 4.78 (d, J=2.2 Hz) ppm.

(3R,4R)-Compound:

$IR_{max}^{CHCl_3}$ (cm$^{-1}$): 1757, 1715, 1600, 1165.

NMR δ(C$_6$D$_6$): 1.16 (3H, d, J=6.6 Hz), 1.79 (3H, s), 3.80 (1H, d, J=2.2 Hz), 4.76 (1H, d, J=2.2 Hz) ppm.

(b)

The same procedure as that described in Example 5a was repeated except that S-(−)-1-phenylethyl glyoxylate was used in place of R-(+)-1-phenylethyl glyoxylate to obtain a mixture of (3S,4S)-1-(di-p-anisylmethyl)-3-acetyl-4-(S-(−)-1-phenylethyloxycarbonyl)-2-azetidinone and (3R,4R)-1-(di-p-anisylmethyl)-3-acetyl-4-(S-(+)-1-phenylethyloxycarbonyl)-2-azetidinone. The NMR spectrum of the mixture was the same as that obtained for the R-(−)-compound and the NMR analysis showed that the proportion of the (3S,4S)-compound and the (3R,4R)-compound was 1:3.

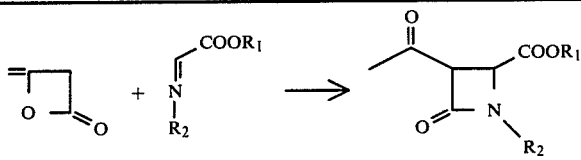

| Example No. | R$_1$ | R$_2$ | Amount of Glyoxylate (Amount of Amine) | Amount of Diketene (Amount of Imidazole) | Reaction Temp. (Dropwise Addition Time) | Reaction Time (Yield) | Spectrum Date of Product |
|---|---|---|---|---|---|---|---|
| 6 | n-Bu | PMP | 2.67 g (1.85 g) | 1.41 g (1.02 g) | 50° C. (2 hrs) | 3 hrs (35%) | IR$^{neat}$: 2955, 1760–1710, 1505, 1236, 1020, 825<br>NMR (CDCl$_3$): 2.40 (3H, s), 3.77 (3H, s), 4.35 (1H, d, J=2), 4.92 (1H, d, J=2) |
| 7 | n-Bu | PMB | 178 mg (137 mg) | 101 mg (68 mg) | 50° C. (20 min.) | 3 hrs (57%) | IR$^{neat}$: 2951, 1760, 1719, 1719, 1610, 1510, 1242, 1175, 1026, 820<br>NMR (CDCl$_3$): 2.30 (3H, s), 3.75 (3H, s) |
| 8 | n-Bu | Bz | 178 mg (107 mg) | 101 mg (68 mg) | 50° C. (20 min.) | 3 hrs (45%) | IR$^{neat}$: 2955, 1760, 1718, 1355, 1205, 1020, 732, 696<br>NMR (CDCl$_3$): 2.33 (3H, s), 7.23 (5H, br. s) |

| Example No. | R$_1$ | R$_2$ | Amount of Glyoxylate (Amount of Amine) | Amount of Diketene (Amount of Imidazole) | Reaction Temp. (Dropwise Addition Time) [Reaction Time] | Yield (Isomer Ratio) | Spectrum Date of Product |
|---|---|---|---|---|---|---|---|
| 9 | CH$_3$–CH–(2-naphthyl) (±) | DAM | 246 mg (243 mg) | 101 mg (68 mg) | 50° C. (20 min.) [1 hr] | 96.8% (ca.2/1)*$^1$ | Isomer 1: IR$^{neat}$: 1750, 1715 (sh), 1603, 1503, 1350, 1172, 1025, 811<br>NMR: 4.00 (1H, d, J=2.2), 4.81 (1H, d, J=2.2)<br>Isomer 2: IR$^{neat}$: 1760, 1718 (sh), 1509, 1356, 1176, 1030, 820<br>NMR: 3.86 (1H, d, J=2.2), 4.80 (1H, d, J=2.2) |
| 10 | CH$_3$–CH–(o-tolyl)–CH$_3$ (±) | DAM | 210 mg (243 mg) | Same as Above | Same as Above | 86% (ca.7/3)*$^1$ | Isomer 1: IR$^{neat}$: 1760, 1710, 1580, 1505, 1458, 1355, 1108, 1028, 820<br>NMR: 3.96 (1H, d, J=2.4), 4.80 (1H, d, J=2.4)<br>Isomer 2: IR$^{neat}$: 1760, 1585, 1506, 1460, 1359, 1180, 1112, 1032, 932, 824<br>NMR: 381 (1H, d, J=2.2), 4.77 (1H, d, J=2.2) |
| 11 | CH$_3$–CH–(o-methoxyphenyl) (±) | DAM | 226 mg (243 mg) | Same as Above | Same as Above | 96% (ca.2/1)*$^2$ | IR$^{CHCl_3}$: 1759, 1715, 1606, 1455, 1353, 1168, 1020,<br>NMR: 1.32, 1.38 (3H, d, J=6.6), 1.85, 1.84 (3H, s), 3.87, 3.98 (1H, d, J=2.4), 4.79, 4.84 (1H, d, J=2.4) |
| 12 | CH$_3$–CH$_2$–CH–Ph (±) | DAM | 210 mg (243 mg) | 101 mg (68 mg) | 50° C. (20 min.) [1 hr] | 89% (ca.4/3*$^2$) | IR$^{CHCl_3}$: 1756, 1718, 1604, 1353, 1168, 1104, 1020<br>NMR: 1.86, 1.80 (3H, s), 3.96, 3.75 (1H, d, J=2.4), 4.79 (1H, d, J=2.4) |

-continued

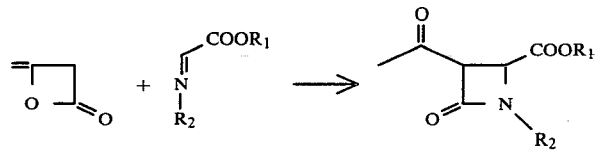

| No. | R₁ | R₂ | | | | | IR/NMR |
|---|---|---|---|---|---|---|---|
| 13 | CH₃-CH-C₆H₄-NO₂ (±) | DAM | 242 mg (243 mg) | 101 mg (68 mg) | 50° C. (20 min.) [1 hr] | 99% (ca.2/1)*² | $IR^{CHCl_3}$: 1753, 1708, 1599, 1497, 1340, 1162, 1100<br>NMR: 1.29, 1.23 (3H, d, J=6.5), 1.90 (3H, s), 3.91 (1H, d, J=2.4), 4.75, 4.71 (1H, d, J=2.4) |
| 14 | CH₃-CH-naphthyl (±) | DAM | 246 mg (243 mg) | 101 mg (68 mg) | 50° C. (20 min.) [1 hr] | 83% (ca.2/1)*² | $IR^{CHCl_3}$: 1755, 1713, 1602, 1350, 1165, 1020<br>NMR: 1.38, 1.34 (3H, d, J=6.4), 1.85, 1.80 (3H, s), 4.00, 3.78 (1H, d, J=2.4), 4.87, 4.85 (1H, d, J=2.4) |
| 15 | Men(l) (−) | PMP | 460 mg (246 mg) | 202 mg (136 mg) | 50° C. (24 min.) [3.5 hrs] | 57% (ca.3/2)*³ | $IR^{neat}$: 2960, 1760, 1722, 1515, 1358, 1250, 1202, 1180, 1160, 1110, 1032, 980, 830, 680<br>NMR: 1.92 (3H, s), 3.23 (3H, s), 4.14, 4.17 (1H, d, J=2.7) |
| 16 | Men(l) (−) | PMB | 230 mg (137 mg) | 101 mg (68 mg) | 50° C. (19 min.) [3.5 hrs] | 63% (ca.3/2)*³ | $IR^{neat}$: 2950, 1760, 1715, 1605, 1505, 1350, 1240, 1210, 1170, 1024, 980, 945, 835, 810, 745<br>NMR: 1.90 (3H, s), 3.27 (3H, s) |
| 17 | Men(l) (−) | Bz | 230 mg (107 mg) | 101 mg (68 mg) | 50° C. (20 min.) [4.5 hrs] | 54% (ca.5/3)*³ | $IR^{neat}$: 2960, 1775, 1720, 1455, 1358, 1218, 1176, 1075, 983, 950, 698<br>NMR: 1.88 (3H, s) |
| 18 | Bor (−) | DAM | 228 mg (243 mg) | 101 mg (75 mg) | 50° C. (50 min.) [2 hrs] | 85% (ca.2/1)*³ | $IR^{CHCl_3}$: 2960, 1760, 1720, 1608, 1510, 1300, 1173, 1028<br>NMR: 1.89 (3H, s), 4.04, 4.02 (1H, d, J=2.4), 4.81, 4.78 (1H, d, J=2.4) |
| 19 | Bor (−) | PMP | 228 mg (123 mg) | 101 mg (75 mg) | 50° C. (20 min.) [2 hrs] | 89% (ca.3/2)*³ | $IR^{CHCl_3}$: 2950, 1750, 1720, 1505, 1440, 1357, 1158, 1110, 1023, 823<br>NMR: 1.89 (3H, s), 4.03, 4.08 (1H, d, J=2.4), 5.07 (1H, d, J=2.4) |
| 20 | Bor (−) | PMB | 228 mg (137 mg) | 101 mg (75 mg) | 50° C. (21 min.) [2 hrs] | 57% (−)*⁴ | $IR^{CHCl_3}$: 2955, 1760, 1723, 1612, 1360, 1110, 1018<br>NMR: 1.90, 1.91 (3H, s), 4.04 (J=2.2), 4.06 (J=2.4)(1H, d) |
| 21 | Cho (−) | DAM | 184 mg (97 mg) | 40 mg (30 mg) | 50° C. (11 min.) [1.5 hrs] | 56% (−)*⁴ | $IR^{CHCl_3}$: 2935, 1760, 1718, 1608, 1455, 1355, 1170, 1020<br>NMR: 1.91 (3H, s), 4.05 (1H, d, J=2.2), 4.80 (1H, d, J=2.2) |
| 22 | CH₃-CHCH₂CH₃ (−) | DAM | 89 mg (146 mg) | 61 mg (45 mg) | 50° C. (21 min.) [2 hrs] | 65% (ca.6/5)*³ | $IR^{CHCl_3}$: 2940, 1760, 1718, 1608, 1458, 1300, 1170, 1108, 1021<br>NMR: 1.88, 1.90 (3H, s), 3.97, 3.99 (1H, d, J=2.2), 4.71, 4.72 (1H, d, J=2.2) |

Note:
(1) The IR spectrum date were given by $IR_{max}$ (cm⁻¹).
(2) The chemical shifts of the NMR spectrum date were given by δ values (ppm), and the coupling constants (J values) were given by the unit Hz. The determination was conducted in $C_6D_6$ unless otherwise indicated.
(3) *¹Yield ratio isolated by silica gel chromatography.
*²Production proportion of R-compound and S-compound calculated from the NMR data.
*³Production proportion of R-compound and S-compound obtained from the NMR data.
*⁴Production proportion of R-compound and S-compound was not determined.
(4) Isomer 1 and Isomer 2 showed the major product and the by-product, respectively.
(5) (+), (−) and (±) in the column R₁ showed optical rotation of the compound represented by the formula R₁OH.

The products obtained in Examples 5 to 22, thereon, can be converted into 3-(1-hydroxyethyl)-2-azetidinone-4-carboxylic acid ester derivatives and the acid derivatives in the same manner as described in Examples 1 to 4.

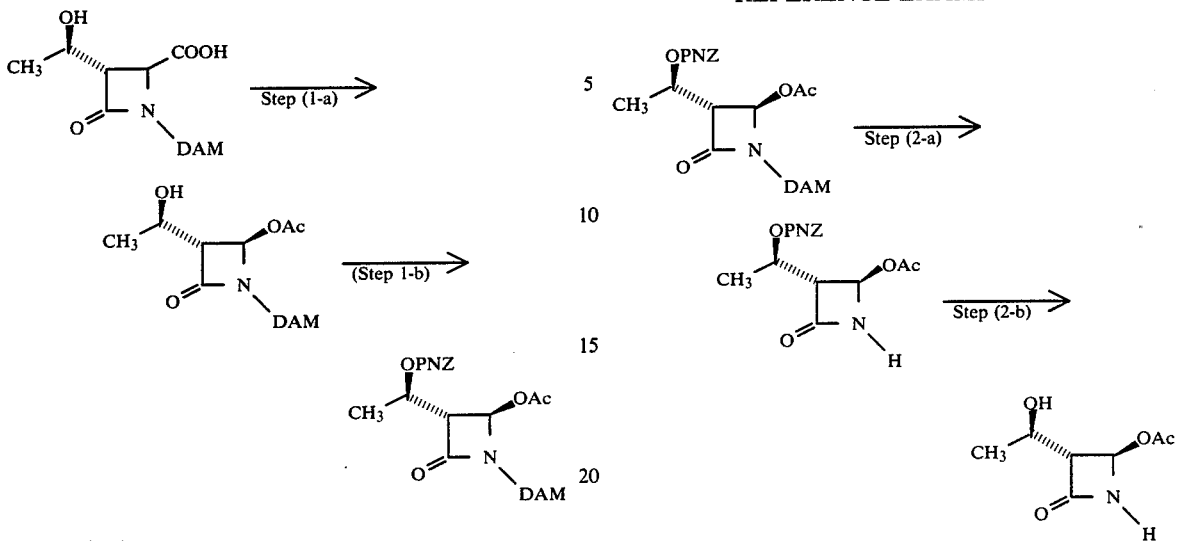

REFERENCE EXAMPLE 2

Step (1-a)
5.3 g of lead tetraacetate was added in several portions at 40° C. to a solution of 4.0 g of (3S,4S,5R)-1-(di-p-anisylmethyl)-3-(1-hydroxyethyl)-4-carboxyl-2-azetidinone and 1.0 g of potassium acetate in 20 ml of dimethylformamide, and the resulting mixture was stirred for 1 hour. Ethylene glycol was added thereto, followed by stirring for several minutes. The reaction mixture was diluted with a saturated aqueous solution of sodium chloride and ethyl acetate. Any insoluble material was filtered, and the filtrate was extracted with ethyl acetate, washed with water and dried over sodium sulfate. The solvent was distilled off, and the residue was purified by silica gel column chromatography to obtain 3.23 g of (3R,4R,5R)-1-(di-p-anisylmethyl)-3-(1-hydroxyethyl)-4-acetoxy-2-azetidinone.

IR$_{max}^{CHCl_3}$ (cm$^{-1}$): 1752, 1357, 1302, 1242, 1174, 1028, 953.

NMR δ(CDCl$_3$): 1.26 (3H, d, J=6.5 Hz), 1.90 (3H, s), 3.07 (1H, broad, d, J=6.5 Hz), 3.78 (6H, s), 4.07 (1H, m), 5.83 (1H, broad, s), 5.88 (1H, broad, s) ppm.

Specific Rotation [α]$_D^{22}$+26.0° (c=0.04, CHCl$_3$).

Step (1-b)
A solution of 1.0 g of (3R,4R,5R)-1-(di-p-anisylmethyl)-3-(1-hydroxyethyl)-4-acetoxy-2-azetidinone in 5 ml of methylene chloride was cooled with ice, and 0.61 g of 4-dimethylaminopyridine was added to the solution. To the resulting mixture was added dropwise a solution of 0.77 g of p-nitrobenzyl chloroformate in 5 ml of methylene chloride. After stirring for 1 hour, 25 ml of toluene was added thereto, and the formed precipitate was removed by filtration. The filtrate was washed successively with 2N hydrochloric acid and a saturated aqueous solution of sodium chloride, dried over sodium sulfate and distilled to remove the solvent.

The resulting residue was purified by silica gel column chromatography to obtain 1.2 g of (3R,4R,5R)-1-(di-p-anisylmethyl)-3-(1-p-nitrobenzyloxycarbonyloxyethyl)-4-acetoxy-2-azetidinone.

IR$_{max}^{neat}$ (cm$^{-1}$): 1770, 1740, 1610, 1583, 1020, 850, 818, 735.

NMR δ(CDCl$_3$): 1.42 (3H, d, J=6 Hz), 1.85 (3H, s), 3.28 (1H, d, J=6 Hz), 3.73 (6H, s), 5.22 (2H, s), 5.87 (1H, s), 6.11 (1H, s) ppm.

Specific Rotation [α]$_D^{22}$+40.5° (c=0.38, CHCl$_3$).

Step (2-a)
5 ml of a 10% water-acetonitrile solution of 1.59 g of ceric ammonium nitrate was added dropwise at room temperature to 10 ml of a 10% water-acetonitrile solution of 0.75 g of (3R,4R,5R)-1-(di-p-anisylmethyl)-3-(1-p-nitrobenzyloxycarbonyloxyethyl)-4-acetoxy-2-azetidinone, and the mixture was stirred for 30 minutes. 1.5 ml of an aqueous solution of 0.05 g of sodium sulfite was added thereto, followed by stirring. The reaction mixture was diluted with a saturated aqueous solution of sodium chloride and extracted with ethyl acetate. The extract was washed successively with a saturated aqueous solution of sodium bicarbonate and a saturated aqueous solution of sodium chloride and dried over sodium sulfate. The solvent was removed by distillation, and the residue was purified by silica gel column chromatography to obtain 0.42 g of (3R,4R,5R)-3-(1-p-nitrobenzyloxycarbonyloxyethyl)-4-acetoxy-2-azetidinone.

IR$_{max}^{neat}$ (cm$^{-1}$): 3300, 1774, 1745, 1602, 1344, 1258, 1029, 843.

NMR δ(CDCl$_3$): 1.45 (3H, d, J=6.0 Hz), 2.09 (3H, s), 3.37 (1H, dd, J=1.2 and 6.0 Hz), 5.25 (2H, s), 5.87 (1H, d, J=1.2 Hz), 6.96 (1H, broad, s) ppm.

Specific Rotation [α]$_D^{22}$+36.6° (c=0.09, CHCl$_3$).

Step (2-b)
300 mg of 5% palladium-on-carbon was stirred in a mixture of 5 ml of ethanol and 5 ml of water in a hydrogen atmosphere for 30 minutes, followed by filtration and washing with water. To the resulting filter cake was added 30 ml of an ethanol solution of 3.00 g of (3R,4R,5R)-3-(1-p-nitrobenzyloxycarbonyloxyethyl)-4-acetoxy-2-azetidinone, and the mixture was stirred for 2 hours in a hydrogen atmosphere. The reaction mixture was filtered using Celite, and the filtrate was concentrated. Silica gel column chromatography of the residue gave 0.900 g of (3R,4R,5R)-3-(1-hydroxyethyl)-4-acetoxy-2-azetidinone.

IR$_{max}^{CHCl_3}$ (cm$^{-1}$): 2980, 1760, 1362, 1220, 1025.

NMR δ(CDCl$_3$): 1.30 (3H, d, J=6 Hz), 2.12 (3H, s), 3.17 (1H, dd, J=2 and 5 Hz), 3.4–3.8 (1H, broad, s), 4.17 (1H, dq, J=5 and 6 Hz), 5.83 (1H, d, J=2 Hz), 7.37 (1H, broad, s) ppm.

While the invention has been described in detail and with reference to specific embodiments thereof, it will be apparent to one skilled in the art that various changes and modifications can be made therein without departing from the spirit and scope thereof.

What is claimed is:

1. A process for producing an N-protected-3-acetyl-2-azetidinone-4-carboxylic acid ester represented by the formula (II):

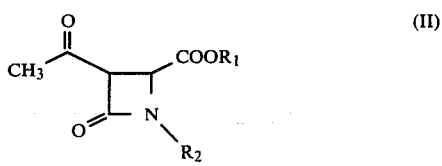

wherein $R_1$ represents a protecting group for a carboxyl group and $R_2$ represents a protecting group for a nitrogen atom, which comprises reacting a Schiff base represented by the formula (I):

wherein $R_1$ and $R_2$ are as defined above, with diketene in an inert solvent in the presence of an imidazole.

2. A process as claimed in claim 1, wherein said protecting group for the nitrogen atom is a di-p-anisylmethyl group.

3. A process as claimed in claim 1, wherein said protecting group for the nitrogen atom is a p-methoxyphenyl group.

4. A process as claimed in claim 1, wherein said protecting group for the nitrogen atom is a p-methoxybenzyl group.

5. A process as claimed in claim 1, wherein said protecting group for the nitrogen atom is a benzyl group.

6. A process as claimed in claim 1, wherein said protecting group for the carboxyl group is an n-butyl, sec-butyl, menthyl, bornyl, cholestenyl, benzyl, 1-phenylethyl, 1-(o-methylphenyl)ethyl, 1-(o-nitrophenyl)ethyl, 1-(o-methoxyphenyl)ethyl, 1-(2,4-dichlorophenyl)ethyl, 1-phenylpropyl, 1-[1]-naphthylethyl or 1-[2]-naphthylethyl group, and said protecting group for the nitrogen atom is a di-p-anisylmethyl, p-methoxybenzyl, p-methoxyphenyl or benzyl group.

7. A process as claimed in claim 1, wherein said protecting group for the carboxyl group is an n-butyl, menthyl, bornyl, 1-phenylethyl, 1-substituted-phenylethyl, 1-[1]-naphthylethyl, or 1-[2]-naphthylethyl, and said protecting group for the nitrogen atom is a di-p-anisylmethyl, p-methoxybenzyl, p-methoxyphenyl or benzyl group.

8. A process for producing an N-protected-3-(1-hydroxyethyl)-2-azetidinone-4-carboxylic acid represented by the formula (IV):

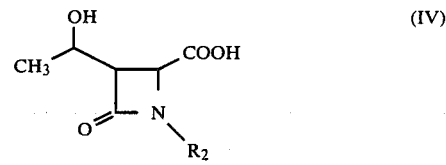

wherein $R_2$ represents a protecting group for a nitrogen atom, which comprises reacting a Schiff base represented by the formula (I):

wherein $R_1$ represents a protecting group for a carboxyl group and $R_2$ is as defined above, with diketene in an inert solvent in the presence of an imidazole to form an N-protected-3-acetyl-2-azetidinone-4-carboxylic acid ester represented by the formula (II):

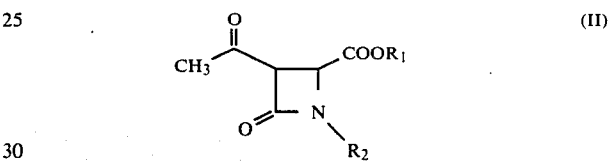

wherein $R_1$ and $R_2$ are as defined above, reducing the acetyl group of the resulting ester to obtain a 3-(1-hydroxyethyl)-2-azetidinone-4-carboxylic acid ester derivative represented by the formula (III):

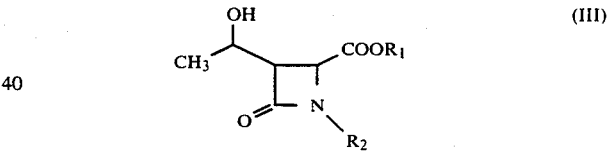

wherein $R_1$ and $R_2$ are as defined above, and removing the protecting group for the carboxyl group $R_1$ from the resulting acetyl derivative of the formula (III).

9. A process as claimed in claim 1 or 8, wherein said protecting group for the carboxyl group is a protecting group having at least one asymmetric carbon atom.

10. A process as claimed in claim 1, wherein said protecting group for the carboxyl group is an alkyl group, an alkenyl group, a substituted lower alkyl group or an aryl group, and said protecting group for the nitrogen atom is a mono- or diarylakyl group or an aryl group.

11. A process as claimed in claim 8, wherein said protecting group for the carboxyl group is an alkyl group, an alkenyl group, a substituted lower alkyl group or an aryl group, and said protecting group for the nitrogen atom is a mono- or diarylakyl group or an aryl group.

* * * * *